United States Patent
Spence et al.

(10) Patent No.: US 8,920,864 B2
(45) Date of Patent: Dec. 30, 2014

(54) SENSATION MASKING COMPOSITION

(75) Inventors: David J. Spence, Rockleigh, NJ (US); Charles Manley, Ringwood, NJ (US); Carter B. Green, Stony Point, NY (US)

(73) Assignee: Takasago International Corporation, Rockleigh, NJ (US)

( * ) Notice: Subject to any disclaimer, the term of this patent is extended or adjusted under 35 U.S.C. 154(b) by 324 days.

(21) Appl. No.: 12/636,339

(22) Filed: Dec. 11, 2009

(65) Prior Publication Data

US 2010/0093869 A1    Apr. 15, 2010

Related U.S. Application Data

(63) Continuation of application No. 11/502,739, filed on Aug. 11, 2006, now abandoned.

(60) Provisional application No. 60/595,874, filed on Aug. 12, 2005.

(51) Int. Cl.
| | | |
|---|---|---|
| A23L 2/56 | (2006.01) | |
| A61K 31/12 | (2006.01) | |
| A61K 9/08 | (2006.01) | |
| A61K 47/22 | (2006.01) | |
| A23L 1/22 | (2006.01) | |
| A23F 3/40 | (2006.01) | |
| A23L 1/226 | (2006.01) | |
| A61K 47/12 | (2006.01) | |
| A23G 4/06 | (2006.01) | |
| A23L 1/221 | (2006.01) | |

(52) U.S. Cl.
CPC . *A61K 9/08* (2013.01); *A61K 47/22* (2013.01); *A23L 1/22066* (2013.01); *A23F 3/405* (2013.01); *A23L 1/22642* (2013.01); *A23L 1/22075* (2013.01); *A23V 2002/00* (2013.01); *A61K 47/12* (2013.01); *A23G 4/06* (2013.01); *A23L 2/56* (2013.01); *A23L 1/221* (2013.01)
USPC ............................. 426/590; 514/689; 514/678

(58) Field of Classification Search
USPC .................................. 424/590; 514/689, 678
See application file for complete search history.

(56) References Cited

U.S. PATENT DOCUMENTS

| | | | |
|---|---|---|---|
| 3,579,353 A | | 5/1971 | Nakel et al. |
| 3,845,134 A | * | 10/1974 | Helmlimger et al. ........... 568/63 |
| 4,459,425 A | | 7/1984 | Amano et al. |
| 4,568,538 A | | 2/1986 | Boden et al. |
| 4,652,682 A | | 3/1987 | Pittet et al. |
| 4,701,336 A | | 10/1987 | Softly et al. |
| 5,545,424 A | | 8/1996 | Nakatsu et al. |
| 5,753,609 A | | 5/1998 | Nakatsu et al. |
| 6,320,069 B1 | | 11/2001 | Sato et al. |
| 6,780,443 B1 | | 8/2004 | Nakatsu et al. |
| 7,030,273 B1 | | 4/2006 | Sun |
| 2002/0119231 A1 | | 8/2002 | Kumamoto et al. |
| 2006/0263475 A1 | | 11/2006 | Jani et al. |
| 2007/0092623 A1 | | 4/2007 | Shimizu et al. |

FOREIGN PATENT DOCUMENTS

| | | |
|---|---|---|
| EP | 0 952 140 | 10/1999 |
| EP | 1 121 927 | 8/2001 |
| EP | 1 163 852 | 12/2001 |
| JP | 57-009729 A | 1/1982 |
| JP | 61 173761 | 8/1986 |
| JP | 04-154719 A | 5/1992 |

OTHER PUBLICATIONS

International Search Report for International Application No. PCT/US06/31585, dated Feb. 21, 2007.
Bezuglov, A., "Vodka with hint of aroma of anise . . . ", Jun. 10, 2004, Derwent Acc. No. 2004-515105, English Abstract.
Database WPI, Week 199415, *Thompson Scientific*, London, GB, AN 1994-123301 and JP 6 070704 (Towa Kasei Kogyo KK) Mar. 15, 1994, XP002660055 (Abstract).
Supplementary European Search Report for EP 06 80 1391, dated Jan. 2, 2012.

* cited by examiner

*Primary Examiner* — Gina C Justice
(74) *Attorney, Agent, or Firm* — Baker Botts L.L.P.

(57) ABSTRACT

The present invention provides masking compositions that include a lower alkyl carboxylic acid, e.g. acetic acid. Also provided is a masking composition that includes (a) a lower alkyl carboxylic acid (e.g. acetic acid), a warming sensate (e.g. vanillin or vanillyl butyl ether) and/or a cooling sensate (e.g. menthol or isopulegol).

19 Claims, No Drawings

US 8,920,864 B2

SENSATION MASKING COMPOSITION

CROSS REFERENCE TO RELATED APPLICATION

This patent application is a continuation of the U.S. Nonprovisional patent application Ser. No. 11/502,739, filed Aug. 11, 2006, which claims the benefit of priority under 35 U.S.C. §119(e) of Provisional Application No. 60/595,874, filed Aug. 12, 2005, which is hereby incorporated by reference in its entirety.

FIELD OF THE INVENTION

The present application relates to compositions that impart a masking effect on the user when orally administered.

BACKGROUND OF THE INVENTION

It is known that substances, including natural isolates, exist which mask undesirable sensations (or tastes) when applied to skin. Topical warming substances are known to provide this masking effect. Substances which provide this masking effect are referred to as "masking agents", "blocking agents", "desensitizing agents", or "numbing agents". Examples of known masking agents include capsicum (red pepper powder, tincture, oleoresin, and extract), capsaicin, homo-capsaicin, homo-dihdrocapsaicin, nonanoyl vanillyl amide, nonanoic acid vanillyl ether, vanillyl alcohol alkyl ether derivatives (JP-A-57-9729), isovanillyl alcohol alkyl ether derivatives, ethylvanillyl alcohol alkyl ether derivatives, substituted benzyl alcohol alkyl ether derivatives, 4-(1-menthoxymethyl)-2-(3'-methoxy-4'-hydroxyphenyl)-1,3-dioxolane and analogs (U.S. Pat. Nos. 5,545,424 and 5,753,609), vanillin propylene glycol acetal, ethylvanillin propylene glycol acetal, ginger extract and oil, gingerol, and gingerone. These masking agents may be added as a single ingredient or as part of a fragrance composition to various products to produce a topical masking effect on the skin or oral cavity.

It is also known that numerous sensation are readily expressed on the outer linings of the human oral cavity due to the abundance of taste receptors. The taste receptors of interest are located in the pharynx and on the larynx regions in the back of the oral cavity and throat. These taste receptors (referred to herein as laryngeal taste receptors) are adapted to detect chemicals that are not saline-like, i.e. salty, and occur in chemosensory clusters. They are responsive to both acidic and bitter agents and it is believed that they are connected to the trigeminal nerve. The pharyngeal nerve controls constriction of the throat muscles. The nerve system of the throat is also responsible for the gag and swallowing reflex. The ability to selectively mask or modulate the nerve responses in the throat would be a useful tool for the flavor chemist and would be useful in a variety of consumer products.

SUMMARY OF THE INVENTION

The present invention provides a masking composition comprising a carboxylic acid represented by the formula

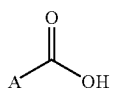

wherein A is a hydrogen, $C_1$-$C_3$ alkyl, or a salt thereof. A preferred carboxylic acid is acetic acid.

The masking composition may further include a warming sensate and/or a cooling sensate along with the carboxylic acid. Preferred warming sensates include vanillyl butyl ether and vanillin. Preferred cooling sensates include isopulegol, 3-(l)-menthoxypropane-1,2-diol and menthol. More preferably, the masking composition contains both a warming sensate and a cooling sensate.

The masking composition may be added to beverages, confections such as gums, tablets, chewy candies or hard candies, and pharmaceutical compositions to mask undesirable or overly intense flavor notes of the substance to which it is added. Also, the masking composition can be used to modulate the nerve responses in the throat and oral cavity upon ingestion of an orally consumable product by adding the masking composition to the product prior to ingestion.

DETAILED DESCRIPTION

An increased masking effect can be provided when a warming sensate is combined with a carboxylic acid.

Carboxylic Acid

Embodiments of the present invention include $C_1$-$C_3$ alkyl carboxylic acids or formic acid that act to mask undesirable or overly intense flavors in products that are orally consumed (e.g. drinks, gums, and liquid pharmaceutical compositions).

As used herein, carboxylic acid refer to compounds represented by the following formula:

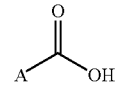

wherein A is a hydrogen, $C_1$-$C_3$ alkyl, or a salt thereof. In embodiments in which A is a $C_2$ or $C_3$ alkyl, the alkyl group may be a straight chain or may be branched. In a preferred embodiment, A is $C_1$ (acetic acid).

Warming Sensates

In one embodiment of the present invention, the warming sensate is selected from compounds represented by the following formula:

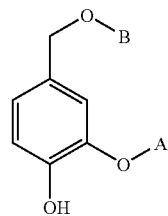

Formula I or an acceptable salt thereof, wherein A is an unsubstituted, branched or straight-chained $C_1$-$C_3$ alkyl group and B is a hydrogen, or an unsubstituted, branched or straight-chained $C_1$-$C_7$ alkyl group.

In one embodiment A is $C_1$ alkyl group. In a preferred embodiment, A is $C_1$ alkyl and B is a $C_2$-$C_4$ alkyl group. In a particularly preferred embodiment, the warming sensate is selected from vanillyl butyl ether (A is a $C_1$ alkyl group and B is a straight-chained, unsubstituted $C_4$ alkyl group) and vanillyl ethyl ether (A is a $C_1$ alkyl group and B is a straight-chained, unsubstituted C₄ alkyl group). Vanillyl butyl ether is commercially available from Takasago, Inc. under the trade name Hotact® VBE.

In another embodiment the warming sensate is selected from compounds represented by the formula:

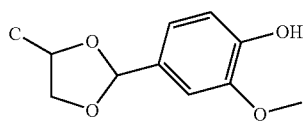

Formula II or a salt thereof wherein C is an unsubstituted, branched or straight-chained $C_2$-$C_8$ alkyl group, optionally interrupted by an oxygen atom.

In a preferred embodiment C is a unsubstituted, straight-chained $C_4$-$C_5$ alkyl group optionally interrupted by an oxygen atom. In a particularly preferred embodiment, warming sensates are selected from vanillin-1,2-hexylene glycol acetal (C is an unsubstituted, straight-chained $C_4$ alkyl group) and vanillin-1-butoxyglycerol acetal (C is an unsubstituted, straight chained $C_5$ alkyl group interrupted by an oxygen at the 2 position). Warming sensates may also be selected from those disclosed in Japanese patent application No. JP 2005-197205, which is hereby incorporated by reference in its entirety.

Warming sensates may also be selected from the group consisting of capsaicin, gingerol, vanillyl ethyl ether, vanillyl propyl ether, vanillyl butyl ether, vanillyl pentyl ether, vanillyl hexyl ether, vanillyl butyl ether acetate, 4-(1-menthoxymethyl)-2-phenyl-1,3-dioxolan, 4-(1-menthoxymethyl)-2-(3', 4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3-dioxolan, 4-(1-menthoxymethyl)-2-(3',4'-methylenedioxyphenyl)-1,3-dioxolan, 4-(1-menthoxymethyl)-2-(3'-methoxy-4'-hydroxyphenyl)-1,3-dioxolan, red pepper oil, red pepper oleoresin, ginger oleoresin, nonylic acid vanillyl amide, jambu oleoresin, Zanthoxylum piperitum extract, sanshool I, sanshool II, sanshoamide, black pepper extract, chavicine, piperine, spilanthol, or those warming sensates disclosed in U.S. Pat. No. 6,780,443, which is hereby incorporated by reference in its entirety.

Cooling Sensates

Embodiments of the present invention also provide a masking composition that includes a cooling sensate along with a carboxylic acid. In preferred embodiments, the masking composition further includes a warming sensate, such as the warming sensates described above.

Examples of cooling sensates that may be included in compositions of the present invention include compounds represented by the formula:

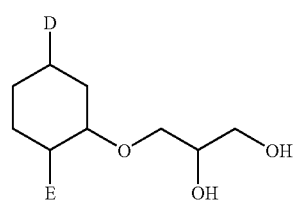

Formula III or salts thereof, wherein D is a straight chained or branched, unsubstituted $C_1$-$C_4$ alkyl or alkenyl group and E is a straight chained or branched, hydroxy-substituted or unsubstituted $C_1$-$C_4$ alkyl group.

In a preferred embodiment, the cooling sensate is represented by the formula:

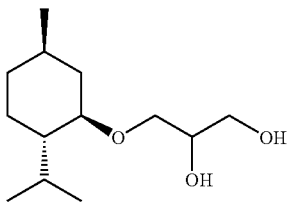 [SMILES: CC(C)[C@@H]1CC[C@@H](C)C[C@H]1OCC(O)CO]

or salts thereof. This compound (3-(l)-menthoxypropane-1,2-diol) is commercially available from Takasago, Inc. under the name Coolact® 10, and is disclosed in U.S. Pat. No. 4,459,425 which is hereby incorporated by reference.

Other cooling sensates which may be included in compositions of the present invention include, but are not limited to, menthol, menthone, camphor, pulegol, isopulegol, cineol, mint oil, peppermint oil or fractions thereof, spearmint oil, eucalyptus oil, 3-l-menthoxypropane-1,2-diol, N-alkyl-p-menthane-3-carboxamide, 3-l-menthoxy-2-methylpropane-1,2-diol, p-menthane-3,8-diol, 2-l-menthoxyethane-1-ol, 3-l-menthoxypropane-1-ol, 4-l-menthoxybutane-1-ol, 1-(2-hydroxy-4-ethylcyclohexyl)-ethanone, menthyl 3-hydroxybutanoate, menthyl lactate, menthone glycerin ketal, 2-(2-l-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, Menthol propylene glycol carbonate; Menthol ethylene glycol carbonate, and 6-isopropyl-3,9-dimethyl-1,4-dioxaspiro[4.5]decan-2-one.

Other cooling senates are disclosed in U.S. Pat. Nos. 7,030,273 and 6,780,443, which are hereby incorporated by reference in their entirety.

Masking Compositions of the Present Invention

The use level of the warming sensate (e.g. vanillyl butyl ether) and carboxylic acid may vary higher or lower depending on the specific product to which the masking composition is applied. Generally, a sensate masking composition is first prepared, which is then added to the composition that is to be consumed. In one embodiment of the present invention, the amount of warming sensate ranges from about 0.001% to about 5.0% by weight, or from about 0.01% to about 0.5% by weight, based on the total weight of the sensate masking composition. The total amount of warming sensate may be decreased by combining a warming sensate with a smaller amount of cooling sensate. This combination can reduce the likelihood of irritation upon ingestion of the composition.

In one embodiment, the use level of the carboxylic acid ranges from about 0.05% to about 10%, of from about 0.5% to about 6%, by weight based on the total weight of the sensate masking composition.

The use level of the sensate masking composition, based on the total weight of the composition to be consumed may also vary. In one embodiment the use level of the sensate masking composition ranges from about 0.001% to 0.25% of the total weight of the consumed composition. In another embodiment, the amount of sensate composition ranges from about 0.01% to about 0.07% based on the total weight of the consumed composition.

The sensate masking composition may be applied to all types of beverages, but particularly beverages that have relatively high acidities such as fruit drunks, and beverages that are known to have intense aftertastes due to, for example, the use of artificial sweeteners, such as diet cola drinks. The sensate masking composition may also be used in confections such as gums (e.g. coated gums), tablets, chewy candy and hard candy. Alternatively, the sensate masking composition may also be used in pharmaceutical products such as cough syrups or other liquid pharmaceutical formulations, chewable tablets or pharmaceutical dosage forms in the form of a "candy", and hard lozenges.

EXAMPLES

The following examples illustrate the invention without limitation.

Example 1

Sensation Masking Composition I

The following components were mixed in the amounts shown in Table 1:

TABLE 1

| Ingredient | Amounts (mL) |
| --- | --- |
| Propylene glycol tincture | 94.840 |
| Menthol, natural | 0.020 |
| Maltol, natural | 0.004 |
| peppermint fraction 10% in EtOH (95%) | 0.030 |
| (l)-menthone, natural | 0.100 |
| Vanillin, natural | 0.002 |
| Takasago St. John's ® Bread extract[1] | 0.004 |
| Glycerin, natural | 5.000 |
| | 100.000 |

[1]Commercially available from Takasago International Corp. (Rockleigh, NJ)

The Sensate Masking Composition I is then prepared by combining the following:

| Composition from Table 1 | 95 parts (by volume) |
| --- | --- |
| Acetic acid, natural[2] | 5 parts (by volume) |

[2]Commercially available from Advanced Biotech (Paterson, NJ)

Example 2

Sensation Masking Composition II

The following components were mixed in the amounts shown in Table 2:

TABLE 2

| Ingredient | Amount (mL) |
| --- | --- |
| Acetic acid (glacial)[2] | 0.75 |
| Hotact ® VBE (Vanillyl butyl ether)[1] | 0.10 |
| Coolact ® P[1] | 0.05 |
| Maltol | 0.10 |
| Furaneol (@20% in EtOH (95%)) | 0.13 |

TABLE 2-continued

| Ingredient | Amount (mL) |
| --- | --- |
| Benzyl alcohol | 10.00 |
| Triglycerides | 88.87 |
| | 100.00 |

[1]Commercially available from Takasago International Corp. (Rockleigh, NJ)
[2]Commercially available from Brown Chemical (Oakland, NJ)

Example 3

Diet Cranberry Raspberry Still Beverage (5% Juice)

The following components were mixed in the amounts shown in Table 3:

TABLE 3

| INGREDIENT | AMOUNT | |
| --- | --- | --- |
| VIS Pectin | 1.60 | gms |
| Sucralose 25% Solution | 0.51 | mls |
| Acesulfame Potassium | 0.07 | gms |
| Sodium Citrate | 0.13 | gms |
| Ascorbic Acid | 0.05 | Gms |
| Citric Acid | 0.50 | Gms |
| Malic Acid | 0.35 | Gms |
| Fumaric Acid | 0.13 | Gms |
| Red Raspberry Juice Conc., 65 brix (2%) | 2.81 | gms |
| Cranberry Juice Conc., 50 brix (2%) | 3.10 | gms |
| White Grape Juice Conc., 68 brix (1%) | 2.51 | gms |
| Red 40, 1% Soln. (w/v) | 2.00 | mls |
| Blue 1, 0.1% Soln. (w/v) | 2.50 | mls |
| Q.S with water to total | 1000.00 | mls |

Brix: 0.83 +/− 0.10
pH: 2.68 +/− 0.10
Pasteurize 190-195° F. for 1-2 minutes.

Takasago Cran-Raspberry Flavor

| Takasago Natural Raspberry Flavor[1] | @0.04% |
| --- | --- |
| Takasago VIVID FL ™ Natural Red Raspberry Flavor[1] | @0.09% |
| Takasago Natural Cranberry Flavor[1] | @0.10% |
| Sensation Masking Composition I (See Example 1) | @0.03% |

[1]Commercially available from Takasago International Corp. (Rockleigh, NJ)

A second control beverage was prepared as described above, except that Sensation Masking Composition I was left out of the beverage.

A sensory panel was formed to evaluate the two diet cranberry/raspberry beverages prepared above. The panel evaluated refrigerated soufflé cups containing 1 oz. of the beverage either with or without the sensate masking composition. Two samples were administered per session in a blind and randomized fashion. Water at room temperature and unsalted crackers were given to the panelist in between samples to cleanse their palate. Each panelist participated in two sessions over two days.

The panelist scored the samples using one of two scales having the following criteria:
Scale #1—"Just About Right" Scale (3=Just About Right) for the following attributes:
    Overall Flavor Strength (Anchored w/Much too weak-Much too Strong)
    Sweetness Intensity (Anchored w/Not At All Sweet-Much Too Sweet)
    Tartness Intensity (Anchored w/Not At All Tart-Much Too Tart)

Bitterness Intensity (Anchored w/Not At All Bitter-Much Too Bitter)

Scale #2—Intensity Scales (9 pt.) for Hedonic (Liking) for the following attributes:

Sweetness Liking (Anchored w/Dislike Extremely-Like Extremely)

Aftertaste Strength (Anchored w/None-Strong;)

Aftertaste Pleasantness (Anchored w/Not At All Pleasant-Extremely Pleasant)

Overall Liking (Anchored w/Dislike Extremely-Like Extremely)

The following averaged results (n=9) were reported by the panel:

| Attribute | Scale # (Best Possible Score for Scale) | Control-Diet CranRasp w/o Sensation Masking Composition I | Diet CranRaspBev w/Sensation Masking Composition I @0.03% |
|---|---|---|---|
| Overall Flavor Strength | 1 (3) | 3.11 | 3.00 |
| Sweetness Liking | 2 (9) | 5.56 | 5.89 |
| Sweetness Intensity | 1 (3) | 3.39 | 3.39 |
| Tartness Intensity | 1 (3) | 2.33 | 2.28 |
| Bitterness Intensity | 1 (3) | 2.28 | 2.44 |
| Aftertaste Strength | 2 (9) | 5.00 | 4.56 |
| Aftertaste Pleasantness | 2 (9) | 5.72 | 6.33 |
| Overall Liking | 2 (9) | 5.78 | 6.39 |

The results for the panel show that the Sensation Masking Composition I improves the "overall flavor strength" slightly (towards "just right") and it decreases the "Aftertaste Strength." "Sweetness and Tartness Intensity" do not seem to be significantly affected by the masking flavor while the "Bitterness Intensity" is improved or shifted towards "just right". The results show a good preference for "Aftertaste Pleasantness", "Overall Liking" and "Sweetness Liking"

Example 4

Tea Beverage

The following components were mixed in the amounts shown in Table 4:

TABLE 4

| INGREDIENT | AMOUNT |
|---|---|
| High fructose corn syrup-55 | 14.00 g |
| Sucrose | 2.00 g |
| Tea Solids | 0.20 g |
| Citric Acid | 0.10 g |

TABLE 4-continued

| INGREDIENT | AMOUNT |
|---|---|
| Takasago Natural Tea Flavor (without natural flavor)[1] | 0.10 ml |
| Water | Q.S. |
| | 100 mL |

Beverage Brix: 12.2 ± 0.2
pH: 3.0 ± 0.2

One beverage was prepared based on Table 4 with 500 ppm of sodium benzoate and 0.05% of Sensation Masking Composition I. A second beverage (control) was prepared with only 500 ppm of sodium benzoate added.

By the protocol described in Example 3, the following averaged results (n=7) were reported by the panel.

| Attribute | Scale # (Best Possible Score for Scale) | Control -- Tea Beverage w/Na Benzoate @ 500 ppm | Tea Beverage w/Na Benzoate @500 ppm and Sensation Masking Composition I @ 0.05% |
|---|---|---|---|
| Overall Flavor Strength | 1 (3) | 2.93 | 3.13 |
| Sweetness Liking | 2 (9) | 5.27 | 5.33 |
| Sweetness Intensity | 1 (3) | 3.87 | 3.80 |
| Tartness Intensity | 1 (3) | 3.00 | 2.80 |
| Bitterness Intensity | 1 (3) | 2.40 | 2.40 |
| Aftertaste Strength | 2 (9) | 4.53 | 4.27 |
| Aftertaste Pleasantness | 2 (9) | 4.87 | 5.07 |
| Overall Liking | 2 (9) | 5.13 | 5.07 |

The results for the panel show that the Sensation Masking Composition I increases the "overall flavor strength" above the "just right" point (3) and it decreased the "Aftertaste Strength". "Sweetness Intensity" is shifted towards "just right" and "Bitterness Intensity" is not affected by the masking flavor while the "Tartness Intensity" is decreased or shifted away from "just right". The results show a good preference for "Aftertaste Pleasantness" and a slight preference for "Sweetness Liking". The results also show a slight preference for control in "overall liking".

Example 5

Tea Beverage

Tea beverages were prepared as described in Example 4, except that potassium sorbate was substituted for sodium benzoate. One beverage was prepared based on Table 4 with 500 ppm of potassium sorbate and 0.05% of Sensation Masking Composition I. A second beverage (control) was prepared with only 500 ppm of potassium sorbate added.

By the protocol described in Example 3, the following averaged results (n=8) were reported by the panel.

| Attribute | Scale # (Best Possible Score for Scale) | Control -- Tea Beverage w/ Potassium Sorbate @ 500 ppm | Tea Beverage w/Potassium Sorbate @500 ppm and Sensation Masking Composition I @ 0.05% |
|---|---|---|---|
| Overall Flavor Strength | 1 (3) | 3.00 | 3.38 |
| Sweetness Liking | 2 (9) | 5.31 | 5.00 |
| Sweetness Intensity | 1 (3) | 3.75 | 3.81 |
| Tartness Intensity | 1 (3) | 2.81 | 2.63 |
| Bitterness Intensity | 1 (3) | 2.25 | 2.44 |
| Aftertaste Strength | 2 (9) | 4.31 | 5.06 |
| Aftertaste Pleasantness | 2 (9) | 5.31 | 4.88 |
| Overall Liking | 2 (9) | 5.25 | 4.94 |

The results for the panel show that Sensation Masking Composition I slightly intensified the "overall flavor strength" and the "aftertaste strength". "Bitterness Intensity" is slightly improved (shifted towards "just right") by the masking flavor while the "Sweetness Intensity" and "Tartness Intensity" are shifted away from "just right". The results show a slight decreased preference for "Aftertaste Pleasantness" and "Overall Liking" compared to control. The sample with Sensation Masking Composition I was preferred for Aftertaste Strength.

Example 6

Tea Beverage

Tea beverages were prepared as described in Example 4, except that sodium hexametaphosphate was substituted for sodium benzoate. One beverage was prepared based on Table 4 with 500 ppm of sodium hexametaphosphate and 0.05% of Sensation Masking Composition I. A second beverage (control) was prepared with only 500 ppm of sodium hexametaphosphate added.

By the protocol described in Example 3, the following averaged results (n=7) were reported by the panel.

| Attribute | Scale # (Best Possible Score for Scale) | Control 3 Tea Beverage w/Na Hexametaphosphate@ 500 ppm | TeaBev w/Na Hexametaphosphate @500 ppm + Sensation Masking Composition I @ 0.05% |
|---|---|---|---|
| Overall Flavor Strength | 1 (3) | 3.07 | 3.00 |
| Sweetness Liking | 2 (9) | 5.71 | 5.00 |
| Sweetness Intensity | 1 (3) | 3.43 | 3.57 |
| Tartness Intensity | 1 (3) | 2.86 | 2.79 |
| Bitterness Intensity | 1 (3) | 2.64 | 2.50 |
| Aftertaste Strength | 2 (9) | 3.64 | 3.93 |
| Aftertaste Pleasantness | 2 (9) | 6.21 | 5.86 |
| Overall Liking | 2 (9) | 6.07 | 5.50 |

The Example 4 results for the panel show that the Sensation Masking Composition I balances the "overall flavor strength" (shifted towards "just right"). "Sweetness Intensity" is increased by the masking flavor, while the "Tartness Intensity" and "Bitterness Intensity" is decreased or shifted away from "just right". The "Aftertaste Strength" is increased with the masking composition, but there is panel preference for "Sweetness Liking" "Aftertaste Pleasantness" and "Overall Liking" for the control sample.

Example 7

Apple Flavored Beverage

The following components were mixed in the amounts shown in Table 5:

| Ingredients | Amounts |
|---|---|
| High Fructose Corn Syrup 55 | 120.00 gms. |
| Apple Juice Concentrate 70 Brix | 17.18 gms. |
| Sodium Benzoate | 0.40 gms. |
| Citric Acid (50% solution w/v) | 5.00 mls. |
| Malic Acid (50% solution w/v) | 5.00 mls. |
| Takasago Vivid Flavors ™ Natural Fuji Apple Flavor WONF[1] | 1.00 mls. |
| Sensation Masking Composition I | 0.55 mls. |
| Water QS to Yield | 1000.00 mls. |

[1]Commercially available from Takasago International Corp. (Rockleigh, NJ)

Finished Product Specifications:
Brix: 10.2
pH: 3.17
Juice Content: 10%

A second control beverage prepared was prepared as described above, except that Sensation Masking Composition was not added.

By the protocol described in Example 3, the following averaged results (n=7) were reported by the panel.

| Attribute | Scale # (Best Possible Score for Scale) | Control-10% Apple Juice Beverage w/o Sensation Masking Composition I | 10% Apple Juice Beverage w/Sensation Masking Composition I @ 0.055% |
|---|---|---|---|
| Overall Flavor Strength | 1 (3) | 2.93 | 2.93 |
| Sweetness Liking | 2 (9) | 6.36 | 6.50 |
| Sweetness Intensity | 1 (3) | 2.93 | 3.07 |
| Tartness Intensity | 1 (3) | 2.71 | 2.50 |
| Bitterness Intensity | 1 (3) | 2.50 | 2.43 |
| Aftertaste Strength | 2 (9) | 4.50 | 4.71 |
| Aftertaste Pleasantness | 2 (9) | 5.21 | 6.29 |
| Overall Liking | 2 (9) | 6.00 | 6.29 |

The results for the panel show that the Sensation Masking Composition I does not alter the "overall strength" perception and it impacts positively the aftertaste strength. "Sweetness Intensity" is increased above the "just right" level slightly and the "Bitterness Intensity and Tartness Intensity are decreased away from the "just right" level by the masking flavor. The results show a good preference for "Sweetness Liking", "Aftertaste Pleasantness" and "Overall Liking". Overall, there is a directional preference for the apple juice with the added Sensation Masking Composition I.

Example 8

Chewing Gum Pellet

A commercial chewing gum pellet with a high (l)-menthol content was chosen as the control sample.

A gum coating slurry was prepared. First an unflavored gum coating slurry having the ingredients shown in Table 6 was prepared:

TABLE 6

| Unflavored Gum Coating Slurry | |
|---|---|
| Sorbitol | 60.00% |
| Water | 34.47% |
| Gum Arabic | 5.13% |
| Titanium Dioxide | 0.40% |
| | 100.00% |

The unflavored slurry (92.5%) was combined with the Sensation Masking Composition II (7.5%) and it was heated until a temporary suspension was achieved, allowed to cool slightly, and the pieces of gum were dipped and allowed to dry overnight. The average coating weight was 0.08 grams which affords an average Sensation Masking Composition II loading of 0.06% on each piece of gum. Coded chewing gum samples were then individually wrapped.

The control chewing gum pellet and chewing gum pellet dipped with the composition containing Sensation Masking Composition II were evaluated by a sensory panel. Two samples were administered per session in a blind and randomized fashion, with a 15 minute break in between samples. Unsalted crackers were given to the panelist in between samples to cleanse their palate.

The following two scales were used by the panelist to evaluate the sample:

Scale #1—"Just About Right" Scales (3=Just About Right) for the following attributes:

Overall Flavor Strength (Anchored w/Much too weak-Much too Strong)

Menthol Intensity (Anchored w/Not At All Menthol-Much Too Menthol)

Bitterness Intensity (Anchored w/Not At All Bitter-Much Too Bitter)

Scale #2—Intensity Scales (9 pt.) for Hedonic (Liking) for the following attributes:

Flavor Impact Liking (Anchored w/Dislike Extremely-Like Extremely)

Overall Liking (Anchored w/Dislike Extremely-Like Extremely)

Aftertaste Menthol Intensity (Anchored w/None-Strong;)

Aftertaste Pleasantness (Not At All Pleasant-Extremely Pleasant)

Overall Aftertaste Liking (Anchored w/Dislike Extremely-Like Extremely)

The following averaged results (n=6) were reported by the panel:

| Attribute | Scale # (Best Possible Score for Scale) | Control Commercial Market gum Sample | Test 1 - Control Commercial Market Sample with Takasago Intensate Natural Flavor - Sensation Masking Composition II @ 0.06% |
|---|---|---|---|
| Overall Flavor Strength | 1 (3) | 4.18 | 3.64 |
| Flavor Impact Liking | 2 (9) | 5.27 | 6.09 |
| Menthol Intensity | 1 (3) | 4.27 | 3.91 |
| Bitterness Intensity | 1 (3) | 4.00 | 4.45 |
| Overall Liking | 2 (9) | 5.36 | 5.82 |
| Aftertaste Menthol Intensity | 2 (1) | 6.91 | 6.55 |
| Aftertaste Pleasantness | 2 (9) | 4.82 | 5.91 |
| Overall Aftertaste Liking | 2 (9) | 5.64 | 6.00 |

The results for the panel show that the Sensation Masking Composition II decreases the "overall flavor strength" perception (from "Much too strong" towards "just right") and it also reduces the "Menthol Intensity" and "Aftertaste Menthol Strength". "Bitterness intensity" was increased with the sensate masking composition sample. The results show a strong preference for "Flavor Impact Liking", "Aftertaste Pleasantness", "Overall Liking" and "Overall Aftertaste Liking" in the flavor containing the masking flavor. Overall, there is a directional preference for the chewing gum with the Sensation Masking Composition II coating.

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

The invention claimed is:

1. An orally consumable masking composition comprising;
(a) between about 0.05% and about 10% by weight of a carboxylic acid represented by the formula

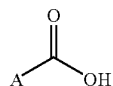

wherein A is a hydrogen, $C_1$-$C_3$ alkyl, or a salt thereof; and
(b) from about 0.001% to about 5% by weight of a warming sensate; and
(c) a cooling sensate.

2. The masking composition of claim 1 wherein the warming sensate is a compound selected from the groups consisting of:
(a) a compound represented by the following formula:

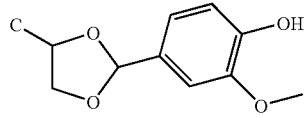

Formula I wherein A is a unsubstituted, branched or straight-chained $C_1$-$C_3$ alkyl group and B is a hydrogen, or an unsubstituted, branched or straight-chained $C_1$-$C_7$ alkyl group, or a salt thereof;
(b) a compound represented by the formula

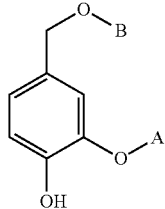

Formula II wherein C is an unsubstituted, branched or straight-chained $C_2$-$C_8$ alkyl group, optionally interrupted by an oxygen atom, or a salt thereof; or
(c) a compound selected from the group consisting of capsaicin, gingerol, vanillyl ethyl ether, vanillyl propyl ether, vanillyl butyl ether, vanillyl pentyl ether, vanillyl hexyl ether, vanillyl butyl ether acetate, 4-(1-menthoxymethyl)-2-phenyl-1,3-dioxolan, 4-(1-menthoxymethyl)-2-(3',4'-dihydroxyphenyl)-1,3-dioxolan, 4-(1-menthoxymethyl)-2-(2'-hydroxy-3'-methoxyphenyl)-1,3-dioxolan, 4-(1-menthoxymethyl)-2-(4'-methoxyphenyl)-1,3-dioxolan, 4-(1-menthoxymethyl)-2-(3',4'-methylenedioxyphenyl)-1,3-dioxolan, 4-(1-menthoxymethyl)-2-(3'-methoxy-4'-hydroxyphenyl)-1,3-dioxolan, red pepper oil, red pepper oleoresin, ginger oleoresin, nonylic acid vanillyl amide, jambe oleoresin, Zanthoxylum piperitum extract, sanshool I, sanshool II, sanshoamide, black pepper extract, chavicine, piperine, and spilanthol.

3. The masking composition of claim 1, wherein the warming sensate is selected from vanillin, ortho-vanillin, ethyl vanillin, vanillyl acetate, vanillyl isobutyrate, capsicum, nonanoyl vanillyl amide, nonanoic acid vanillyl ether, vanillyl alcohol alkyl ether, isovanillyl alcohol alkyl ether, ethylvanillyl alcohol alkyl ether, isovanillyl alcohol alkyl ether, ethylvanillyl alcohol alkyl ether, substituted benzyl alcohol alkyl ether, 4-(1-menthoxymethyl)-2-(3'-methoxy-4'-hydroxyphenyl)-1,3-dioxolane, vanillin propylene glycol acetal, ethylvanillin, propylene glycol acetal, ginger extract, ginger oil, gingerol, gingerone, and analogs and derivatives of the above.

4. The masking composition of claim 1, wherein the warming sensate is vanillyl butyl ether.

5. The masking composition of claim 1, wherein the warming sensate is vanillin.

6. The masking composition of claim 1, wherein the cooling sensate is selected from the group consisting of

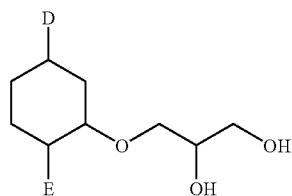

Formula III (a) a compound represented by the formula:
or salts thereof, wherein D is a straight chained or branched, unsubstituted $C_1$-$C_4$ alkyl or alkenyl group and E is a straight chained or branched, hydroxy-substituted or unsubstituted $C_1$-$C_4$ alkyl or alkenyl group; and
(b) a compound selected from the group consisting of menthol, menthone, camphor, pulegol, isopulegol, cineol, mint oil, peppermint oil, spearmint oil, eucalyptus oil, 3-l-menthoxypropane-1,2-diol, N-alkyl-p-menthane-3-carboxamide, 3-l-menthoxy-2-methylpropane-1,2-diol, p-menthane-3,8-diol, 2-l-menthoxyethane-1-ol, 3-l-menthoxypropane-1-ol, 4-l-menthoxybutane-1-ol, 1-(2-hydroxy-4-ethylcyclohexyl)-ethanone, menthyl 3-hydroxybutanoate, menthyl lactate, menthone glycerin ketal, 2-(2-l-menthyloxyethyl)ethanol, menthyl glyoxylate, N-methyl-2,2-isopropylmethyl-3-methylbutanamide, menthyl 2-pyrrolidone-5-carboxylate, monomenthyl succinate, alkali metal salts of monomenthyl succinate, and alkali earth metal salts of monomenthyl succinate, monomenthyl glutarate, alkali metal salts of monomenthyl glutarate, alkali earth metal salts of monomenthyl glutarate, N-[[5-methyl-2-(1-methylethyl)cyclohexyl]carbonyl]glycine, p-menthane-3-carboxylic acid glycerol ester, menthol propylene glycol carbonate; menthol ethylene glycol carbonate, and 6-isopropyl-3,9-dimethyl-1,4-dioxaspiro[4.5]decan-2-one.

7. The masking composition of claim 4, wherein the cooling sensate is selected from menthol, 3-(l)-menthoxypropane-1,2-diol, and isopulegol.

8. The masking composition of claim 1, further comprising
(a) propylene glycol;
(b) menthol;
(c) maltol;
(d) peppermint or a peppermint fraction;
(e) (l)-menthane;
(f) vanillin;
(g) a carob extract; and
(h) glycerin.

9. The masking composition of claim 1, further comprising
(a) vanillyl butyl ether;
(b) isopulegol;
(c) maltol;
(d) furaneol;
(e) benzyl alcohol; and
(f) triglycerides.

10. A beverage comprising the masking composition of claim 1.

11. A confection comprising the masking composition of claim 1.

12. The confection of claim 11 in the form of a gum, tablet, chewy candy or hard candy.

13. A pharmaceutical composition comprising the masking composition of claim 1.

14. A method of masking undesirable or overly intense flavor notes of a beverage, food or orally consumable product comprising adding to the beverage, food or orally consumable product the orally consumable masking composition of claim 1.

15. A method of modulating the nerve responses in the throat and oral cavity upon ingestion of an orally consumable product comprising adding to the orally consumable product the orally consumable masking composition of claim 1.

16. The masking composition of claim 1, wherein the carboxylic acid is acetic acid.

17. The masking composition of claim 5, wherein the cooling sensate is selected from methol, 3-(l)-menthoxypropane-1,2-diol and isopulegol.

18. The method of claim 14, wherein the carboxylic acid is acetic acid.

19. The method of claim 15, wherein the carboxylic acid is acetic acid.

* * * * *